United States Patent [19]

DeBush

[11] Patent Number: 5,613,497
[45] Date of Patent: Mar. 25, 1997

[54] MINIATURE PEAK FLOW METER

[75] Inventor: George DeBush, Hamden, Conn.

[73] Assignee: The D & T, Inc., Hamden, Conn.

[21] Appl. No.: 367,574

[22] Filed: Jan. 3, 1995

[51] Int. Cl.$^6$ .................................... A61B 5/09
[52] U.S. Cl. ............... 128/726; 128/725; 73/861.76; 482/13
[58] Field of Search .................. 128/725–727; 73/861.74–861.76; 482/13

[56] References Cited

U.S. PATENT DOCUMENTS

| | | | |
|---|---|---|---|
| 2,889,707 | 6/1959 | Snider | 73/861.76 |
| 3,797,480 | 3/1974 | Williams | 128/726 |
| 4,041,935 | 8/1977 | Garbe | 128/727 |
| 4,638,812 | 1/1987 | Hakkinen | 128/726 |
| 5,224,487 | 7/1993 | Bellofatto et al. | 128/725 |
| 5,253,651 | 10/1993 | Stockwell et al. | 128/725 |
| 5,277,195 | 1/1994 | Williams | 128/725 |

*Primary Examiner*—Lee S. Cohen
*Attorney, Agent, or Firm*—Stroock & Stroock & Lavan

[57] ABSTRACT

Miniature peak flow meter is compact, portable diagnostic device of beeper size. It consists of two bodies which create a curved cylinder inside which moves a rotational piston by means of rotation. The resistance to that movement is achieved by a specially created torsion spring. The mouthpiece is folded inside the device in unused position thus contributing to the compactness. By pulling out the mouthpiece and blowing through it, the patient rotates the piston by his expiratory flow and moves a pointer secured in a groove on the top side of the device. The pointer shows the value on a printed scale, and the patient writes it on a recording chart placed on the bottom surface of the device.

22 Claims, 9 Drawing Sheets

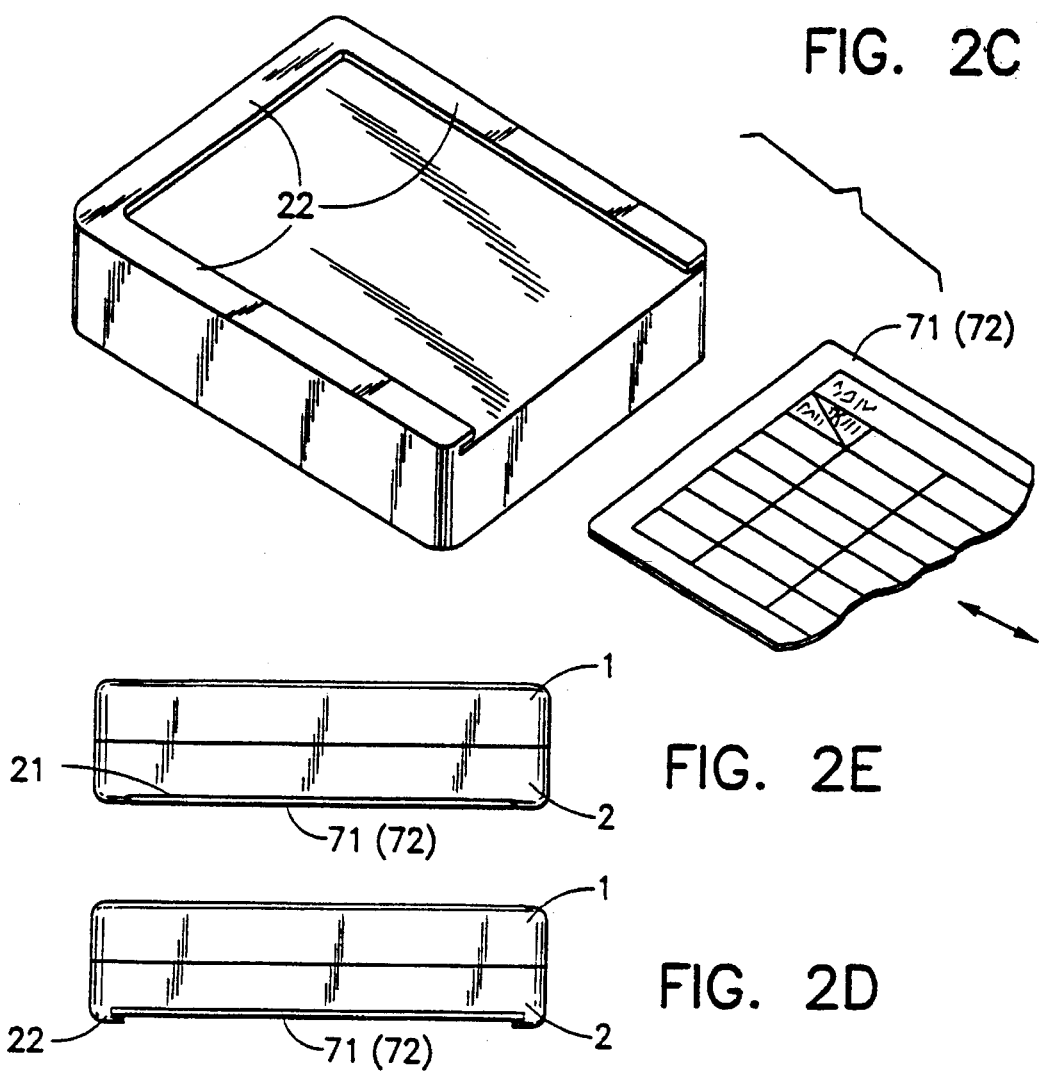
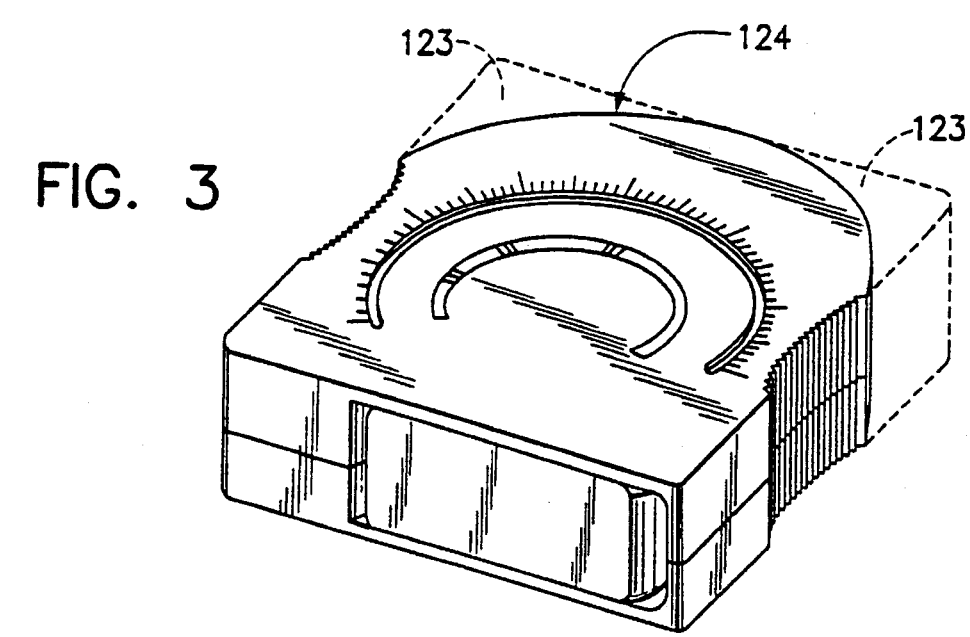

5,613,497

MINIATURE PEAK FLOW METER

BACKGROUND OF THE INVENTION

The present invention deals with a mechanically constructed portable device commonly known in the pulmonary field as the peak expiratory flow meter, and, more specifically, with a device that is compact, portable and can fit into a very small purse or pocket.

In the management of pulmonary diseases, and particularly in the management of asthma, it is very common to monitor the patients' peak expiratory flow rate by means of peak flow meters. Most pulmonary patients are supposed to monitor their peak expiratory flow several times a day, record it, and present the data to their physicians on a regular basis. Furthermore, patients may experience a shortness of breath caused by a certain activity or a change in medication. In order to avoid a false alarm and panic, the value of peak expiratory flow is used as one of the first and reliable indicators of lung performance. In both regular and emergency monitoring the patient has to have a peak flow meter readily available: in a purse or a pocket. Often the patient wants a socially acceptable device that doesn't obviously suggest a medical instrument, as well as a device that doesn't require multiple actions in for example, preparation for use or to record the reading.

In accordance with the National Heart, Lung and Blood Institute guidelines mechanical peak flow meters have to be accurate over a full range to ±10%, the reproducibility being ±5% and interdevice variability being ±5%. When we add ease of viewing, size, manufacturing cost, ease of cleansing, and ease of recording a rather complex set of problems arises, some of them contradictory. Neither today's market nor patent art have a single mechanical peak flow meter which satisfies all of these requirements. This invention is the first one that addresses and fulfills all of them.

Although many mechanical peak flow meters are labeled as "portable" and "friendly" to use, they do not in fact satisfactorily meet these requirements. There is a need for a beeper-size device with approximate dimensions of 2⅞"× 2¼"×⅝". The device described in U.S. Pat. No. 5,224,487 which claims to be the smallest and is marketed as such, has the dimensions of 6⅜"×2"×⅞". Its volume is almost three times the volume of the device according to this invention; when it is unfolded and ready to use, its volume is even greater. It also contains one loose piece.

SUMMARY OF THE INVENTION

Although the mechanical peak flow meters seem to be relatively simple, they need to fulfill multiple requirements, sometimes contradictory ones. This is why the existing peak flow meters are, from a technical standpoint, compromise solutions.

One of the first and biggest advantages of the peak flow meter according to this invention is its true portability because of its beeper size.

The main portion of the peak flow meter, its body, contains a long, curved channel inside which a piston moves frictionlessly. This piston actually rotates around a pivot which is placed outside of the curved channel. The rotational piston and its pivotal shaft are connected with the body through a torsion spring or springs which give resistance to the patient's expiratory flow. The top of the device has a large groove (for example, more than 180 degrees) inside of which moves a slidable pointer. When the patient blows into the device, the spring yields and the piston rotates to a certain position. The pointer is pushed by the piston inside its groove. After the blowing action, the piston moves back to initial position and the pointer stops and indicates the measured volume on the scale which is printed on the top outside surface. After the reading, the pointer is also moved to initial position, ready for the new measurement.

Although absolute size is very important, the peak flow meter according to this invention offers other features.

The accuracy, reproducibility and interdevice variability of this invention far exceed the guidelines set by the National Heart, Lung, and Blood Institute. This is achieved by the frictionless piston, and the minimal, predictable, and reproducible friction of the pivot. The specially engineered frictionless torsion spring contributes to predictable resistance and once the device is calibrated, the reproducibility is assured.

Another feature of the peak flow meter according to this invention is the mouthpiece, pivoted and folded into the device when not in use. This not only contributes to the compactness of the whole device, but also protects the mouthpiece from dirt (on fingers, pocket, bag, etc.) when not in use.

Another advantageous characteristic of this invention is a large scale for viewing. The length of the pointer groove is about 4½" which provides a stretched scale and consequently the comfort of easy reading.

All existing mechanical peak flow meters are accompanied by a booklet, fairly large in size, in which a patient records the value of measurements whenever the device is used and which is presented to the physician at the next visit. In other words, a patient has to carry both a peak flow meter, which is fairly unwieldy, and a recording booklet. This invention offers among other features another very useful one: while the top surface has a scale and a pointer that serve for visual monitoring of the patient's performance, the whole bottom surface of 2⅞"×2¼" is used for a large chart where the patient can record the measured values. The chart can be sufficient to record a full week of monitoring activities. A device according to this invention does not necessarily call for elimination of the recording booklet, but the patient has the option of transferring the data into the booklet once a week in the comfort of his or her home.

The recording feature on the back side of the peak flow meter is yet another feature. There are two possible variations of this feature. The recording chart can be permanently glued to the back surface of the device and its surface will allow writing. After a week of recording and after the data is transcribed into a booklet, the data on the chart is erased and ready for a new week of recording. Another possibility is to use insert charts. They can be written on on both sides, i.e. used for two weeks, and the patient can bring the physician the filled-out charts instead of a booklet.

The health care industry is very sensitive to the cost of peak flow meters. The peak flow meter according to this invention is basically constructed of five simple and small plastic pieces and one stainless steel spring, and requires few very simple actions to assemble them. Since the plastic pieces are injection molded, this device is very economical to manufacture.

In addition, no maintenance is necessary. Cleaning with cold or hot water and detergent can be done without compromising the performance of the device.

BRIEF DESCRIPTION OF THE DRAWINGS

In the drawing:

FIG. 2C is a perspective view of the bottom of the device with the optional slide-in disposable chart feature FIG. 2D is a side view of the the device shown in FIG. 2C.

FIG. 2E is a similar view showing a different embodiment of the device for attaching the charts.

FIG. 3 is a perspective view of a yet smaller device with rounded corners

DETAILED DESCRIPTION OF THE INVENTION

Figure 1:
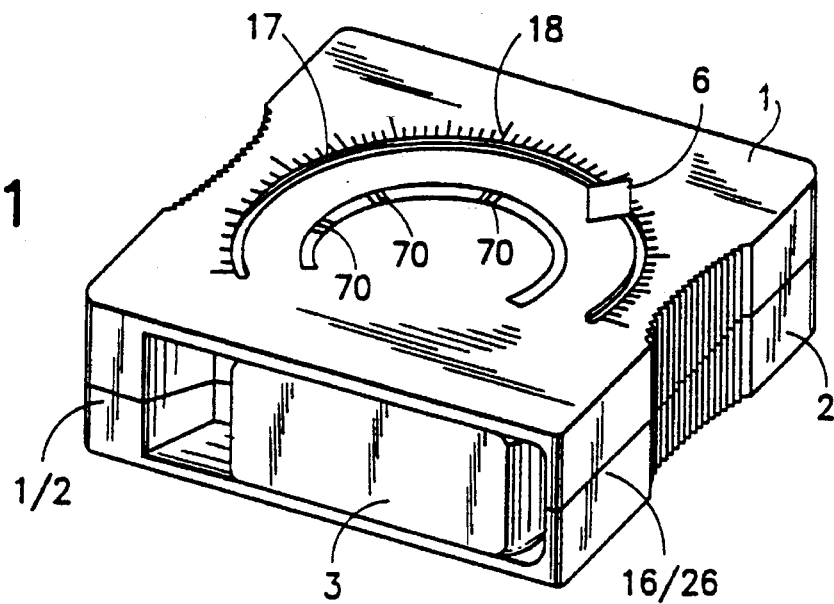
FIG. 1 is a the perspective view of the whole device in storage position with the mouthpiece folded inside

FIG. 1 shows the basic construction and shape of a peak flow meter according to the invention. Its shape and size is the so-called beeper size, with approximate dimensions of 2⅞"×2¼"×⅝". The device is made basically out of six pieces, top body 1, bottom body 2, mouthpiece 3, rotational piston 4, spring 5 (FIG. 5) and pointer 6. The top surface has the groove 17 inside which is placed pointer 6 that can slide with very little constant resistance, so it can stay in any position in the groove, and also be easily moved by finger to the initial position. On the top surface is also placed or imprinted the curved scale 18. The scale is shown on the upper side of the groove 17, but it certainly can be placed on its opposite side. The bodies 1 and 2 are made out of injection molded plastic and after insertion or assembly the interior parts 3, 4 and 5 are joined together on surface ½ by means of screws, glueing, sonic welding or snapping.

Figure 1A:
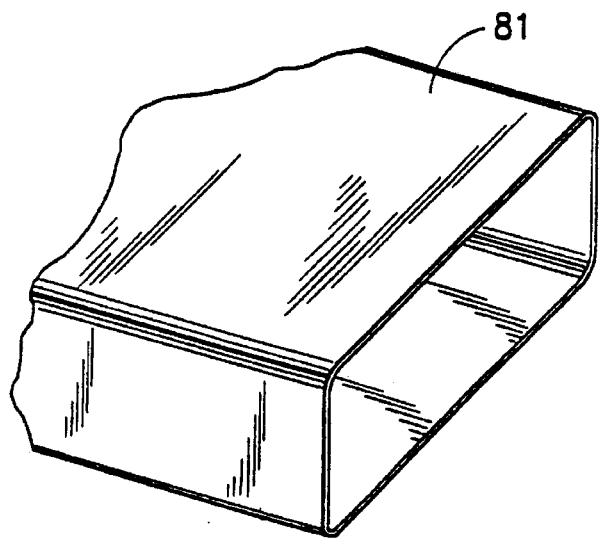
FIG. 1A is a similar view showing the optional rigid plastic case
Figure 1B:
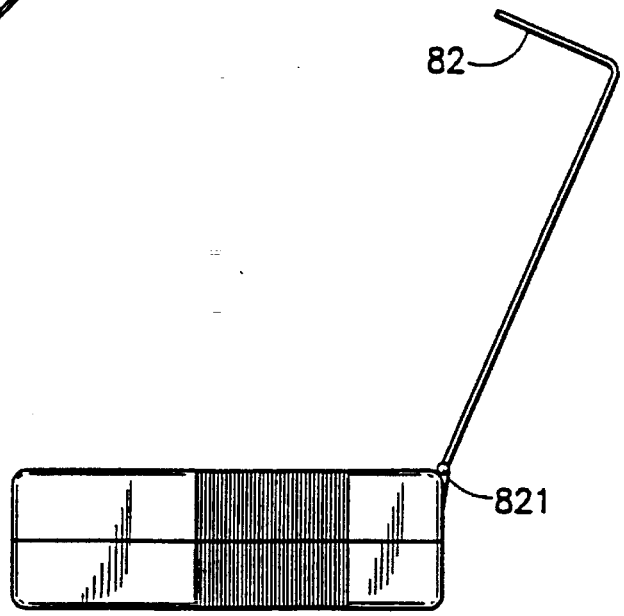
FIG. 1B is a the side view of the device with the optional hinged cover FIG. 2, A and B, are plan views showing the basic shape of the recording charts

The whole device can have an optional hard plastic case 81 (FIG. 1A), open on both sides or on one side only. Another option is to have the cover 82 which is hinged to the top body 1 via hinge 821 (FIG. 1B).

On both sides gripping grooves 16/26 are made which not only assure good gripping by fingers, but also suggest in a no-nonsense way how to use the device. The surface where 16/26 are placed can be slightly indented.

Figures 2A, 2B:
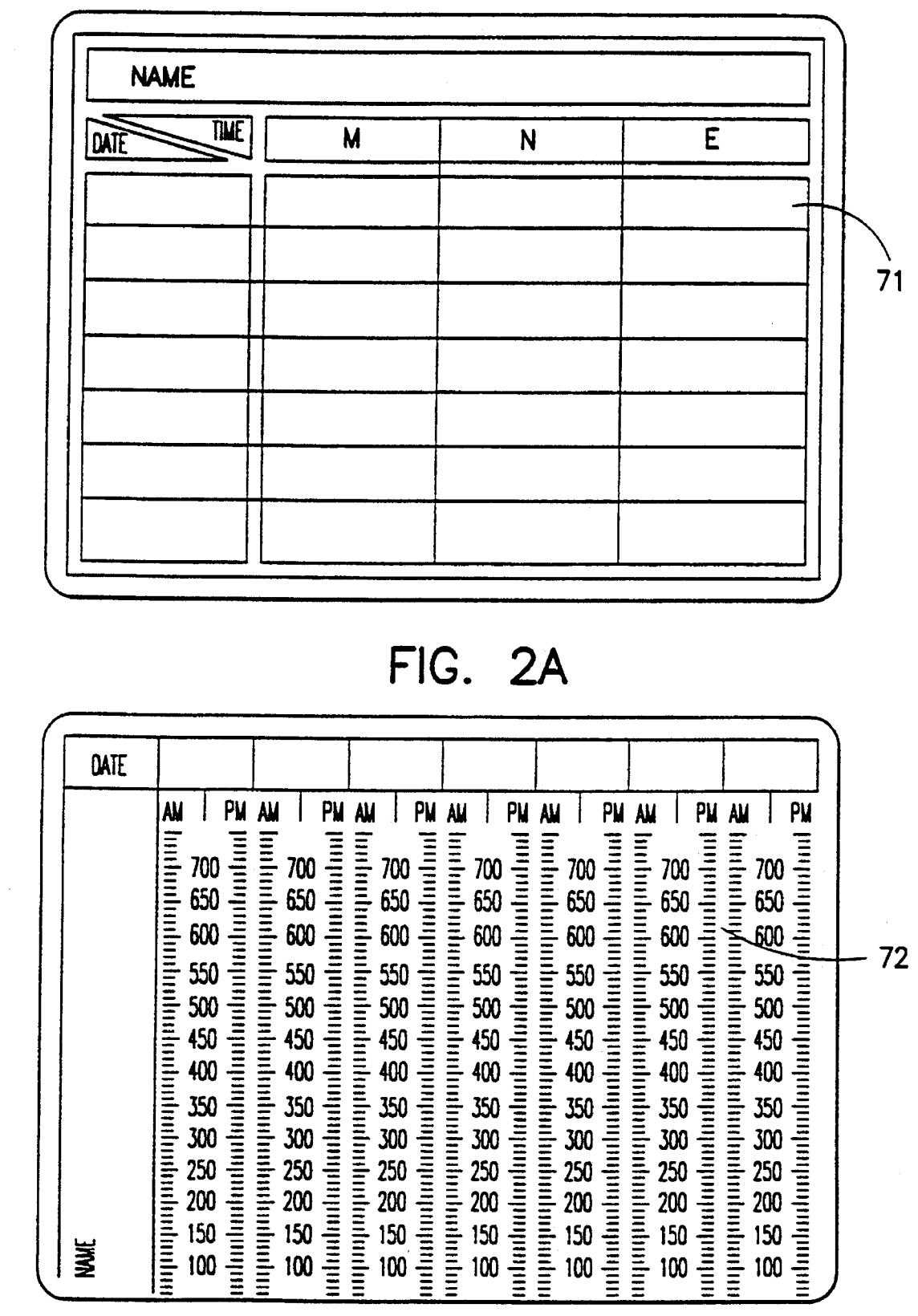

The bottom body 2 can optionally house the recording chart. The patient can either enter the value in l/min for the chosen date and time (FIG. 2A) or can mark the already scaled chart for the date and time (FIG. 2B).

FIGS. 2C, 2D and 2E illustrates two proposed shapes of the recording chart. On the surface 21 of part 2 the chart can be painted or permanently glued as shown in FIG. 2E. On the exposed surface a person can write. The trace of ink can be removed or erased only by firm pressing and wiping with a piece of cloth or cotton, or can be simply washed with warm water and be ready for the next recording. Another embodiment (FIGS. 2C and 2D) shows the bottom body 2 having a lip 22 on at least two opposite sides and a semi-disposable chart can be slid and temporarily locked on the bottom surface. Its advantage is that a person can permanently write on both sides, collect the semi-disposable charts and present them to the physician when visiting.

Although the present peak flow meter in its beeper size is miniature as far as its absolute dimensions and volume are concerned, another embodiment of it has an even lesser volume inside the same overall dimensions, as shown in FIG. 3. Two "dead" corners 123 can be eliminated and a part of the outside shape can be made in the shape of a curve 124, concentric with the groove 17.

Figure 4A:
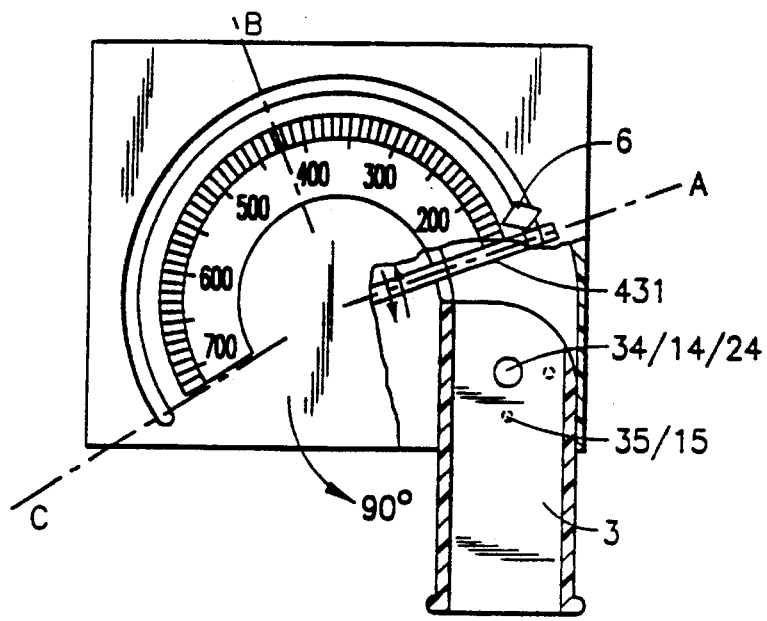
FIG. 4A is a top plan view of the deice showing the pulled-out mouthpiece ready for use
Figure 5:
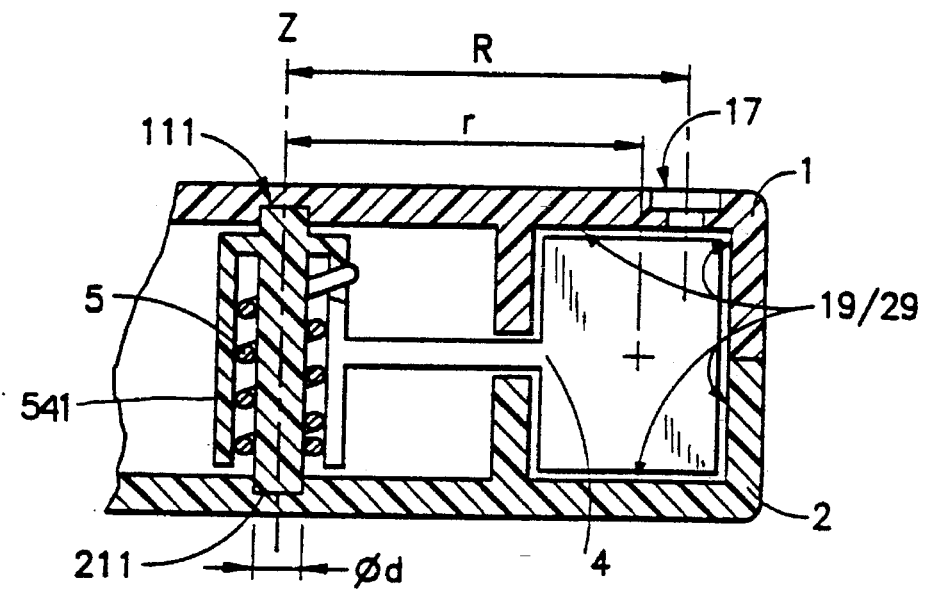
FIG. 5 is a partial sectional view through the center of the device and one half of: the device

FIG. 4A and 5 show the basic function of the device. The mouthpiece 3 is rotated 90 degrees out from inside the device where it was in its stored, not-in-use position. The bodies 1 and 2 create a rectangular channel 19/29 inside which 431, part of which is a rotational piston 4 (FIG. 6), can freely, frictionlessly move. Pointer 6 is immediately behind 431 which is in initial position A. The whole part 4 can rotate around axis Z. Its maximal movement is from point A to point C which represent, but are not limited to, more than 180 degrees. This also represents the full scale of measurement. Mechanical peak flow meters are usually made in two ranges: 100–400 l/min and 100–700 l/min. Since in engineering of the present invention the only variable resistance is solving the force of spring 5, it is feasible that two above mentioned ranges are achieved by simply using a spring with the appropriate spring rate, while the rest of the whole device can be the same. Of course, an appropriate scale should accompany the chosen spring. This certainly can greatly contribute to the economy of producing two different products.

When a patient blows air through the mouthpiece 3, the stream of blown air moves 431 inside 19/29. The resistance to this stream is the force of the spring 5. The final position B of the piston's part 431 and consequently the position of the pointer 6 which is pushed by 431 depends on the "strength" of the patient's air stream.

Spring 5 is lightly prestressed in initial position A. In any other position between A and C the spring stress and consequently accumulated force is larger than at initial position. When a patient's stream stops and there is no more energy to move 431 further, the spring simply moves it to initial position A. But pointer 6 stays in position B and indicates the patient's effort. After reading it, and recording the reading in the chart, the patient moves the pointer 6 with a finger, with minimal effort, to initial position as well and the device is ready for another measurement.

Figure 4B:
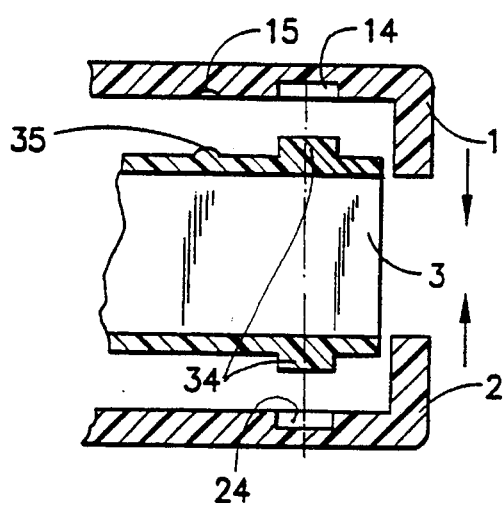
FIG. 4B is an exploded cross-section view through assembled bodies and mouthpiece
Figure 4D:
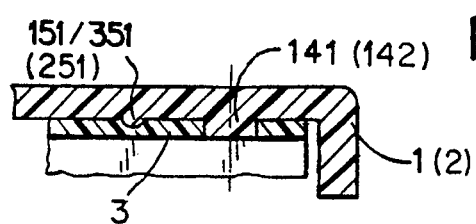
FIG. 4D is a partial sectional view showing another embodiment of the device
Figure 4C:
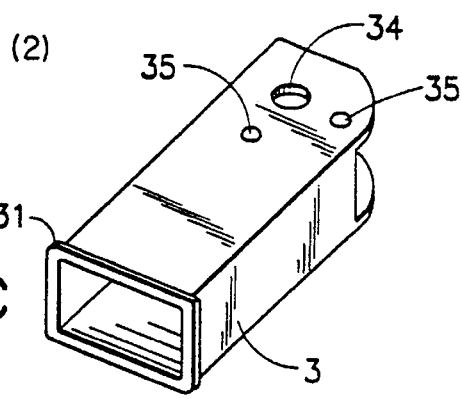
FIG. 4C is a perspective view of the mouthpiece before assembly

FIG. 4B and 4C show some construction details of mouthpiece 3 and appropriate parts of bodies 1 and 2. The entrance of the mouthpiece is supplied with a lip 31, but does not necessarily have to be that way. If a larger entrance cross-section is required, lip 31 can be omitted. Short plastic pins 34 are integrally molded with 3, while two appropriate indentations 14 and 24 are molded in bodies 1 and 2. During assembly, the mouthpiece is sandwiched between bodies and can rotate from closed to opened position. It is convenient that the mouthpiece is locked in these two positions. Simple and inexpensive locking is easy to achieve in such a case. Of numerous possibilities, one simple way is described, but not limited to, here. The mouthpiece has integrally molded bumps 35, two on one side or on both sides. The upper body has a female feature in the shape of indentation 15. When, by rotating the mouthpiece 3, any of the bumps 35 meet 15, a sound can be heard and locking is achieved. As shown in FIG. 4D shows, both features, the molded pins and the male bumps can be reversed. The pins 141 and bump(s) can be part of the body (or bodies), while holes 341 and female indentation(s) 351 can be molded in the mouthpiece 3.

Similarly, FIG. 5 shows that the rotational piston is sandwiched between bodies 1 and 2. As presented in FIG. 5, bodies 1 and 2 have inmolded cylindrical indentations 111 and 211 where male pins 411, FIG. 6, fit and rotate. Of course, just as mouthpiece 3, piston 4 can be sandwiched in so that inmolded pins protrude from bodies 1 and 2 and that the rotational piston has a hole, FIG. 5B. All in all, the goal is to secure a minimum predictable and repeatable friction between swinging elements.

Figure 6:
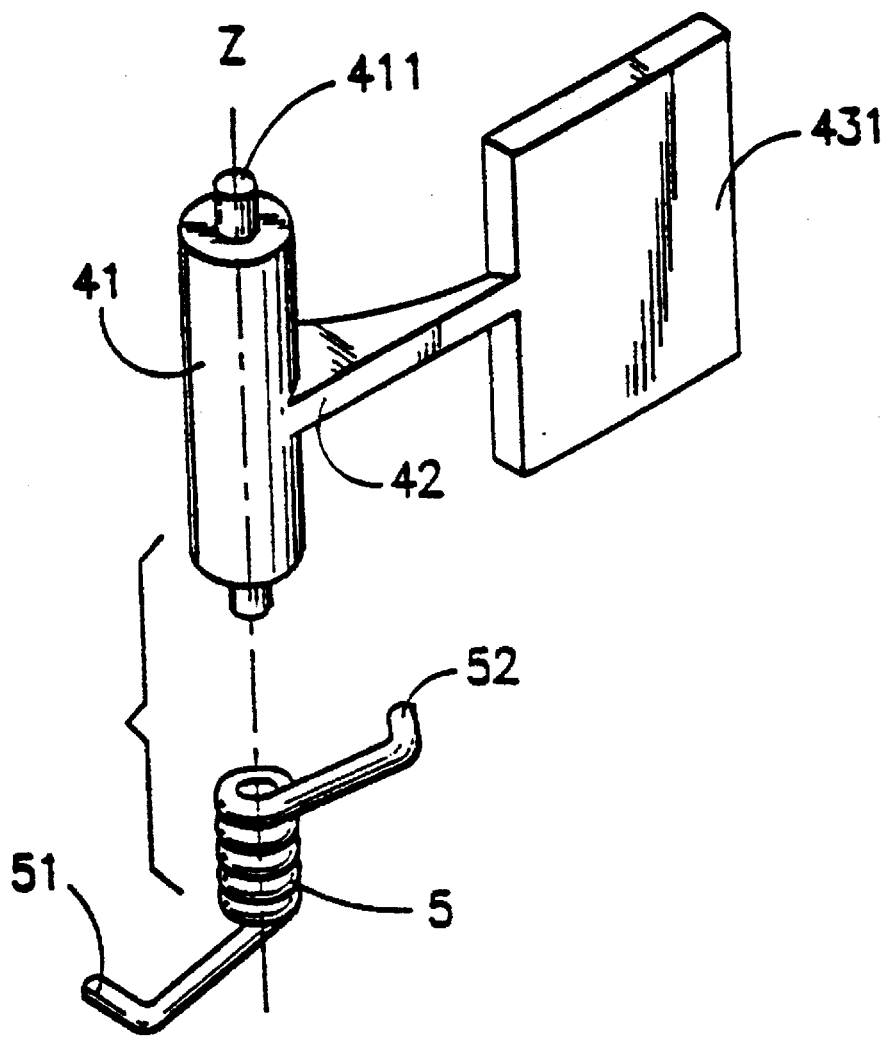
FIG. 6 is a perspective view of the rotational piston and the spring
Figure 6A:
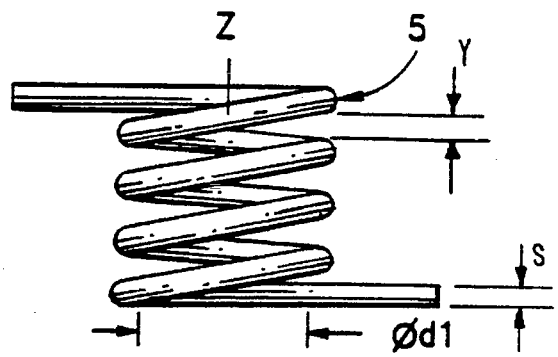
FIG. 6A is an enlarged elevational view of the spring.

FIG. 6 shows the preferable embodiment of the shape of the rotational piston 4. It consists of cylindrical body 541 which houses spring 5, piston surface 431, connector 42, and the pin(s) 411. All the mentioned elements are an integral part of 4; 4 is one, injection molded, plastic piece.

Although it is possible to use a standard torsion spring, the invention suggests the use of a special spring 5. The main features of such a spring would be that the inside diameter of the spring d1 is slightly larger (5–15%) than the appropriate diameter of pin d. Also, it is recommended that a small gap Y (0.010"–0.025") be made between the coils. Both of these measures are aimed at reducing the friction between the spring and the pin and between coils during the accepting of the load while the patient blows into the device. This will greatly contribute to accuracy, reproducibility and reduce interdevice variability.

The end 51 of spring 5 fits to a molded groove in body 2 or 1, while the other end 52 is hooked to a molded groove in 4, so that when 4 is sandwiched between bodies 1 and 2, a slight prestress of 5 is achieved.

FIG. 5 also shows that groove 17 doesn't necessarily have to be placed at the geometrical center of 431. It means that "R" can be different than "r". If a long groove is desired, R>r, and scale 18 is placed between the axes Z and R, but if a large scale 18 is desired that fits above 17, like in FIG. 1, then R becomes smaller and possibly even smaller than r.

Figure 5A:
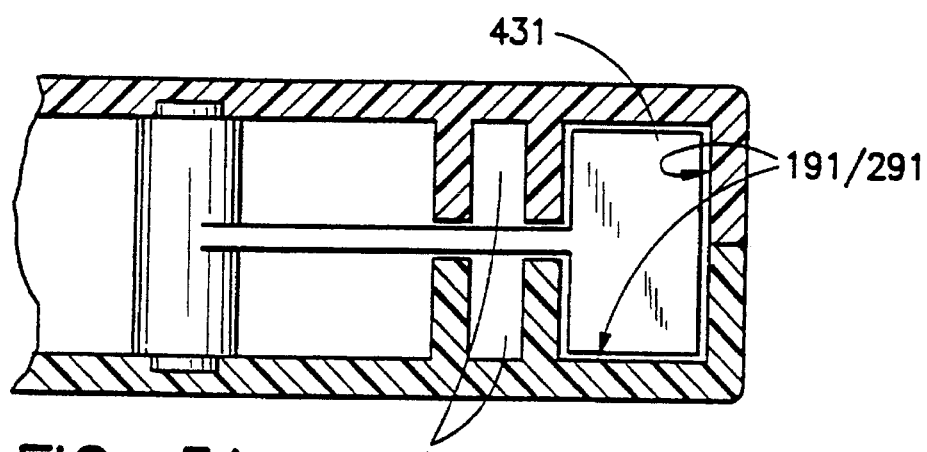
FIG. 5A is a sectional view of another device with a secondary channel

FIG. 5A illustrates another embodiment of the channel where piston 4 is placed. The channel can be divided and form spaces 191/291 and 110/210. As shown in FIG. 7, the mouthpiece covers both channels. One part of the stream pushes 431, while the other flows freely to exit 121 (FIG. 7), and further to exhaust at opening 12. The volume of space 110/210 is about 0–40% of 191/291 and can contribute to minimizing the dimensions of the device.

Figure 5B:
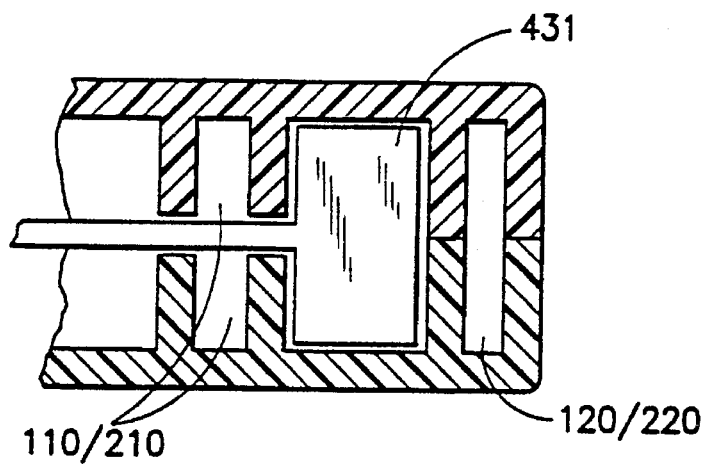
FIG. 5B is a partial cross-section view through another embodiment of the device illustrating the plurality of secondary channels

FIG. 5B shows yet another embodiment of the device. For further minimizing of the device as well as for balancing the air flow, two secondary channels can be introduced, one from each side of the channel 19/29, i.e. secondary channels 110/210 and 120/220.

Figure 7A:
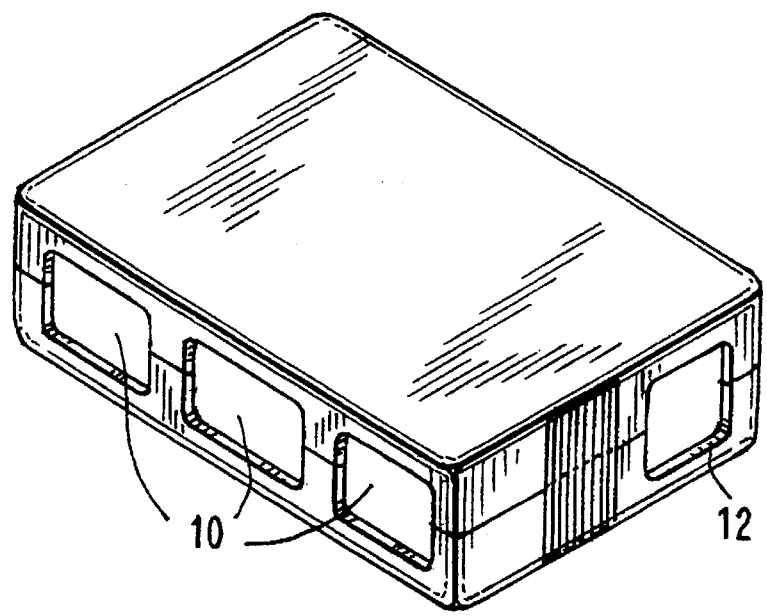
FIG. 7A is a perspective view of the rear part of the device showing some air openings.
Figure 7:
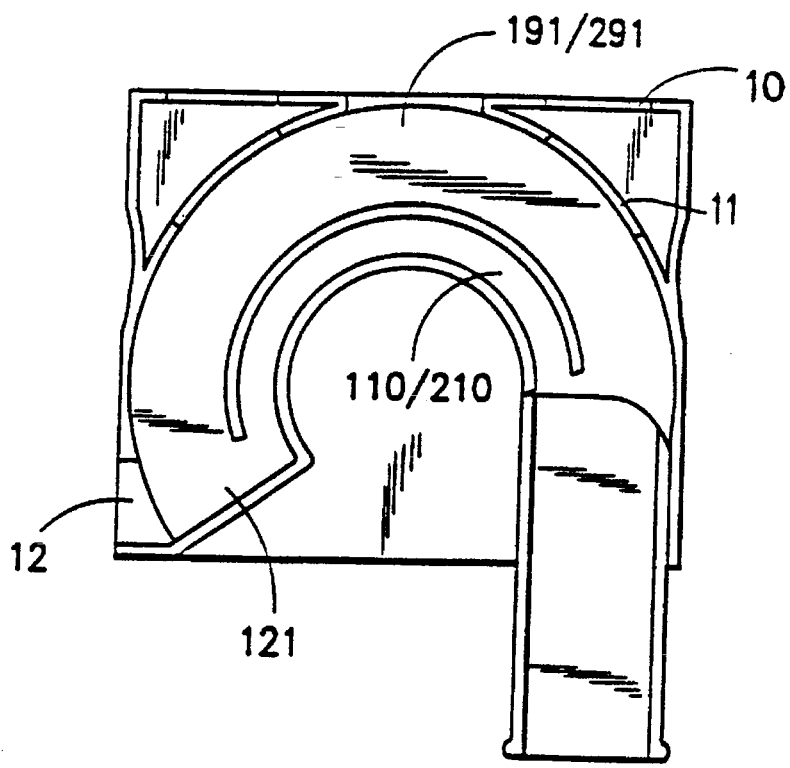
FIG. 7 is a cross-section view that shows a secondary channel and air openings

To achieve sensitivity and accuracy of the device, as well as linearity of the scale 18, openings 11 and 10 are introduced (FIG. 7 and 7A). For better understanding it is important to be aware of the way of approaching the problem. The flow dynamic calculation is performed first which defines the basic geometry of the piston, channel, and the spring rate. Although the invention calls for construction with minimum friction, some friction does exist between the moving parts. Non-linear spring rate of torsion spring is also present. In preproduction stage all of that has to be compensated for by adding the space 110/210 and openings 11 and consequently 10. The number and the size of 11 and 10, the size of 110/210, the number of coils 5, the wire size "s" of 5, and d1 are varied and the device is calibrated.

Figure 6B:
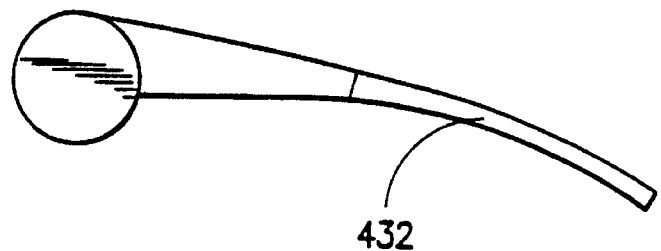
FIG. 6B is a top view of an alternative shape of the rotational piston
Figure 6C:
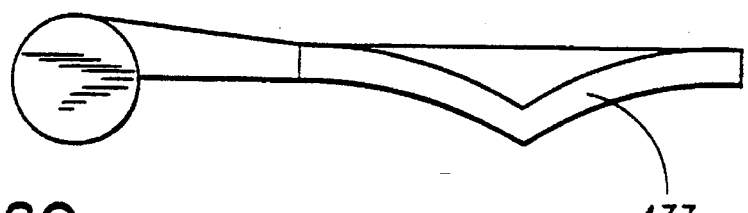
FIG. 6C is a similar view of another alternative shape of the piston.
Figure 6E:
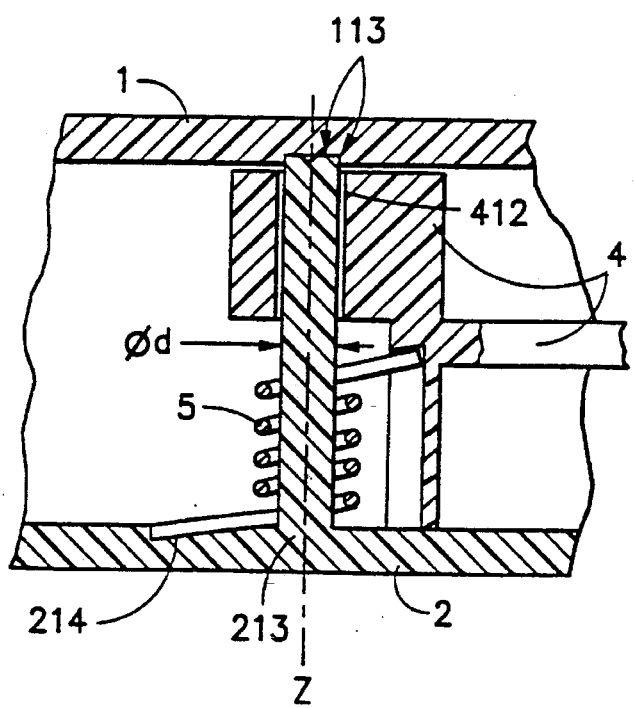
FIG. 6E is a similar view showing yet another embodiment.

FIGS. 6B and 6C shows other embodiments of the rotational piston 4. Basically, the air contact surface can adopt the shape 432 or 433.

Figure 6D:
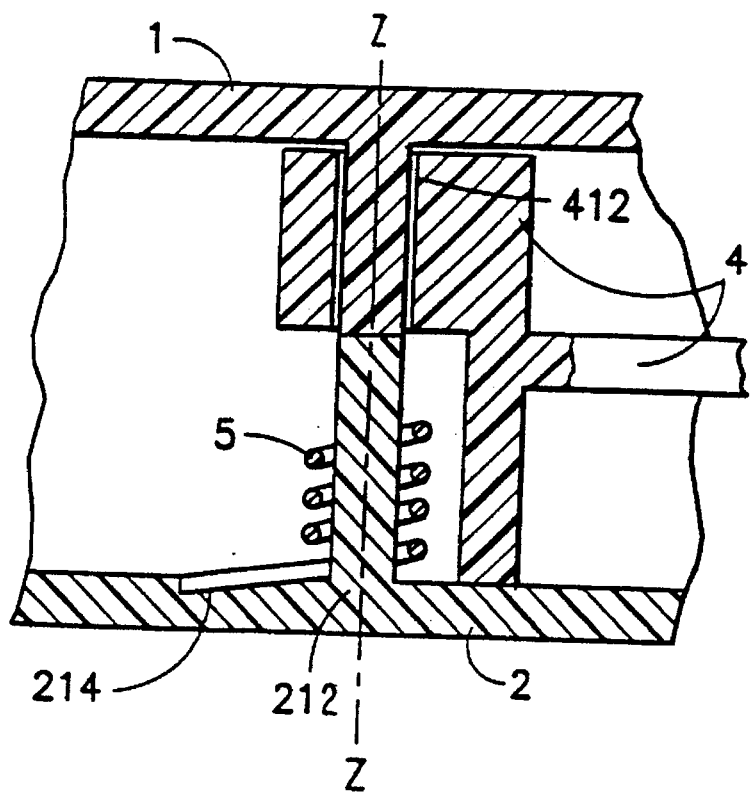
FIG. 6D is a sectional view of the device showing another embodiment of the sandwiched center part of the rotational piston

FIG. 6D illustrates another embodiment of the device where piston 4 has a hole 412 and bodies 1 and 2 have protruding inmolded pins 112 and 212. When assembled, all pins and a hole fall into the same axis Z which is the center of rotation. One logical consequence is that one of the bodies does not have a pin but rather a nest. For instance, if the assembly starts from the bottom body 2, spring 5 is placed first on pin 213 and engaged with inmolded groove 214, then 4 is put on the pin 213 and engaged with the other end of 5; 1 is placed on top and 113 is engaged with 213. Of course, before placing 1, the mouthpiece 3 is put in its place.

Figure 8:
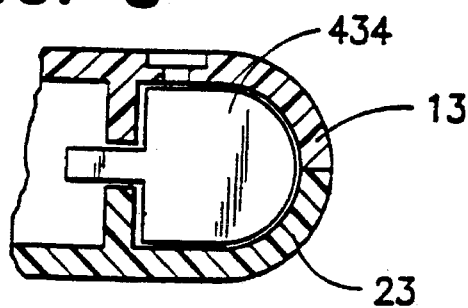
FIGS. 8, 8A and 8B are partial sectional views showing some alternative, but feasible shapes in case a further reduction in size and weight is required
Figure 8A:
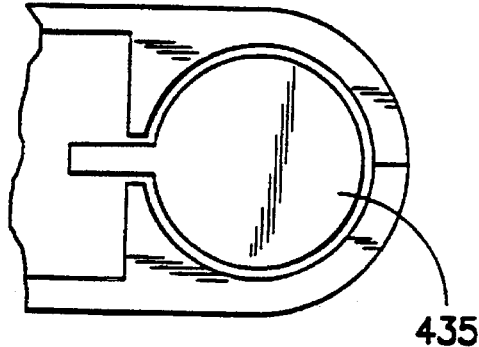
Figure 8B:
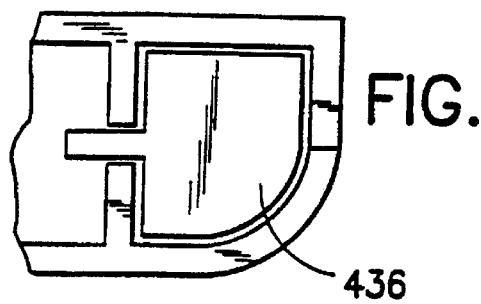

In FIGS. 8, 8A and 8B some other embodiments of shapes of basic form of 431 are shown. The shapes 434, 435, and 436 can be easily achieved. Of course, the bodies 1 and 2 will consequently follow the shape of 4 and always leave a gap for frictionless swinging of piston 4.

I claim:

1. A miniature peak flow meter comprising, in combination:

a hollow body having a top surface;

a curved hollow cylinder disposed within said body, said cylinder having an opening;

a mouthpiece affixed to said body and adapted to direct a flow of fluid into said cylinder through said opening;

a piston movably mounted within said cylinder, said piston having a size and shape such that said piston fits freely inside said cylinder with enough clearance between said piston and said cylinder to allow said piston to move substantially frictionlessly along said cylinder;

means for rotationally mounting said piston about an axis extending through said body, the arrangement being such that said piston rotates concentrically through said cylinder when impacted by said fluid flow;

a spring mounted between said body and said rotatable mounting means, said spring biasing said piston in a direction towards said opening; and a pointer mounted within said top surface, said pointer being free to move along a defined path by rotation of said piston in said cylinder, whereby upon impact of said fluid flow said piston rotates from a rest position to a peak flow position causing said pointer to move along said path until it stops at a point indicating peak fluid flow, said spring forcing said piston to return to its rest position while said pointer remains in place along said path indicating peak fluid flow.

2. A miniature peak flow meter according to claim 1, wherein said path is defined by a curved groove in said top surface which is concentric with said curved cylinder, said groove and said cylinder having a common center located at said axis of rotation and wherein said pointer is mounted within said groove in contact with said piston, said piston moving said pointer along said groove upon impact with said fluid flow.

3. A miniature peak flow meter according to claim 2, wherein a scale is provided along side said groove for measuring the peak fluid flow indicated by said pointer, said scale being concentric with said groove.

4. A miniature peak flow meter according to claim 3, wherein said hollow body includes side walls a portion of which are open to accommodate said mouthpiece, said mouthpiece being rotatably mounted within said open portion so that said mouthpiece can be stored inside said body when not in use and then rotated outwardly to an operative position communicating with said cylinder opening for directing a flow of fluid thereto.

5. A miniature peak flow meter according to claim 4, wherein said body is provided with means for locking said mouthpiece in both said stored and operative positions.

6. A miniature peak flow meter according to claim 3, wherein said body includes a bottom surface and wherein a recording chart is affixed to said bottom surface for recording measurements of said peak fluid flow.

7. A miniature peak flow meter according to claim 6, wherein said recording chart is glued or painted onto said bottom surface.

8. A miniature peak flow meter according to claim 6, wherein said bottom surface is provided with lips on at least two opposite sides thereof, said lips creating straight grooves inside of which a semi-disposable recording chart is removably positioned for recording measurements of said peak fluid flow.

9. A miniature peak flow meter according to claim 1, wherein said means for rotationally mounting said piston comprises a central post mounted for rotation about said axis, an elongated connecting member affixed at one end to said central post and at the other end thereof to said rotating piston, said connecting member passing freely through a slot in said curved cylinder.

10. A miniature peak flow meter according to claim 9, wherein said spring is a torsion spring having a plurality of cylindrical coils and including two opposite ends, said coils being mounted about said axis with one of said opposite ends affixed to said body and the other of said opposite ends affixed to said central post.

11. A miniature peak flow meter according to claim 10, wherein said plurality of coils are made from wire having a predetermined diameter, said coils being separated from each other by gap of about 20 to 50 percent of said wire diameter, thereby providing a substantially frictionless, uniform response to a load applied thereto.

12. A miniature peak flow meter according to claim 9, wherein said hollow body includes a top and bottom section, said central post being formed with integrally molded pins at opposite ends while said top and bottom sections have inmolded cylindrical holes with diameters slightly larger than the diameter of said pins and create bearing surfaces, both said holes and said pins aligning along the same axis which is perpendicular to said top surface of said body and parallel to said axis of rotation.

13. A miniature peak flow meter according to claim 9, wherein said hollow body includes a top and bottom section, said central post being formed with a cylindrical hole while at least one of said top and bottom sections are formed with a cylindrical pin that protrudes through said hole in said central post; said cylindrical hole and said pin creating bearing surfaces, both said hole and said pin aligning along the same axis which is perpendicular to said top surface of said body and parallel to said axis of rotation.

14. A miniature peak flow meter according to claim 1, wherein said curved cylinder has an exit located within a side wall of said body and wherein at least one curved secondary passage is provided on at least one side of said cylinder, said passage having an exit opening located proximate to said exit of said cylinder.

15. A miniature peak flow meter according to claim 14, wherein said mouthpiece directs said flow of fluid to both said cylinder and said secondary passage, the part of said flow of fluid directed through said secondary passage mixing with ambient air blown ahead by said piston while moving in said cylinder.

16. A miniature peak flow meter according to claim 15, wherein said curved cylinder is provided with openings for allowing said blown air to escape, the size and position of said openings being such as to ensure accuracy, repeatability and linearity of said device.

17. A miniature peak flow meter according to claim 16, wherein said body includes a plurality of openings for communicating with said openings in said cylinder allowing part of said blown air to escape while the remainder of said air passes through said exit of said cylinder.

18. A miniature peak flow meter according to claim 1, wherein said hollow body includes a top and bottom section which, when assembled, sandwich together said rotational piston, said spring and said mouthpiece within the interior of said body in a permanently closed unit.

19. A miniature peak flow meter according to claim 18, wherein said top and bottom sections have inmolded pins while said mouthpiece has inmolded holes on opposite sides thereof, said pins and said holes aligning along the same axis which is perpendicular to said top surface of said body and parallel to said axis of rotation.

20. A miniature peak flow meter according to claim 18, wherein said top and bottom sections have inmolded holes while said mouthpiece has inmolded pins on opposite sides thereof, said pins and said holes aligning along the same axis which is perpendicular to top surface of said body and parallel to said axis of rotation.

21. A miniature peak flow meter according to claim 1, wherein the shape of both said cylinder and said rotatable piston is selected from the group consisting of rectangular, circular, semi-circular and rectangular with at least one rounded corner.

22. A miniature peak flow meter according to claim 1, wherein the surface of said rotatable piston is curved in either the radial direction or the direction substantially normal to said piston.

\* \* \* \* \*